(12) United States Patent
McDonald et al.

(10) Patent No.: US 9,510,936 B2
(45) Date of Patent: Dec. 6, 2016

(54) STENT ELEMENT

(75) Inventors: Gary Peter McDonald, Glasgow (GB); David Granville Stevenson, Bridge of Weir (GB)

(73) Assignee: VASCUTEK LIMITED, Renfrewshire, Strathclyde (GB)

( * ) Notice: Subject to any disclaimer, the term of this patent is extended or adjusted under 35 U.S.C. 154(b) by 146 days.

(21) Appl. No.: 14/123,649

(22) PCT Filed: Jun. 1, 2012

(86) PCT No.: PCT/GB2012/051236
§ 371 (c)(1),
(2), (4) Date: Dec. 3, 2013

(87) PCT Pub. No.: WO2012/164294
PCT Pub. Date: Dec. 6, 2012

(65) Prior Publication Data
US 2014/0114393 A1    Apr. 24, 2014

(30) Foreign Application Priority Data
Jun. 3, 2011   (GB) .................................. 1109317.6

(51) Int. Cl.
*A61F 2/06*   (2013.01)
*A61F 2/07*   (2013.01)
(Continued)

(52) U.S. Cl.
CPC .. *A61F 2/07* (2013.01); *A61F 2/86* (2013.01); *A61F 2/89* (2013.01); *A61F 2002/075* (2013.01);
(Continued)

(58) Field of Classification Search
CPC ................ A61F 2/07; A61F 2/86; A61F 2/89; A61F 2002/075; A61F 2230/006
See application file for complete search history.

(56) References Cited

U.S. PATENT DOCUMENTS 4,580,568 A   4/1986 Gianturco
5,720,776 A   2/1998 Chuter et al.
(Continued)

FOREIGN PATENT DOCUMENTS

EP   0686379 A2   12/1995
EP   0880949 A1   12/1998
(Continued)

OTHER PUBLICATIONS

United Kingdom Intellectual Property Office Search Report dated Sep. 27, 2012 for GB1209841.4.
(Continued)

*Primary Examiner* — Robert Lynch
(74) *Attorney, Agent, or Firm* — Heslin Rothenberg Farley & Mesiti P.C.; John W. Boger

(57) ABSTRACT

There is provided a stent element comprising a central portion with two arms extending therefrom, optionally in a V-shaped or Y-shaped configuration. The arms of the stent-element are resiliently deformable to facilitate packing and suitable material for forming the stent-element is nitinol or PEEK. The stent element can be used to stabilise two adjacent ring stents on a stent graft by attachment to the graft material between the ring stents, for example by sewing. The stent element stabilises the ring stent without risk of fracture. A stent graft having two ring stents and the stent element located between the ring stents is also described.

32 Claims, 3 Drawing Sheets

Figure 1:
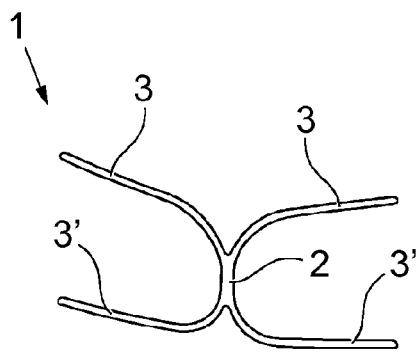

(51) Int. Cl.
  *A61F 2/86* (2013.01)
  *A61F 2/89* (2013.01)
(52) U.S. Cl.
  CPC .. *A61F 2230/006* (2013.01); *A61F 2230/0054* (2013.01); *Y10T 29/49826* (2015.01)

(56) References Cited

U.S. PATENT DOCUMENTS

| | | | |
|---|---|---|---|
| 6,203,568 | B1 | 3/2001 | Lombardi et al. |
| 6,278,079 | B1 | 8/2001 | McIntyre et al. |
| 6,635,080 | B1 | 10/2003 | Lauterjung et al. |
| 2002/0123790 | A1 | 9/2002 | White et al. |
| 2003/0040790 | A1 | 2/2003 | Furst |
| 2006/0155359 | A1* | 7/2006 | Watson ............ A61F 2/07 623/1.13 |
| 2006/0259137 | A1 | 11/2006 | Artof et al. |
| 2008/0114398 | A1 | 5/2008 | Phillips et al. |
| 2008/0161909 | A1 | 7/2008 | Kheradvar et al. |
| 2009/0005848 | A1* | 1/2009 | Strauss ............ A61F 2/91 623/1.2 |

FOREIGN PATENT DOCUMENTS

| | | |
|---|---|---|
| EP | 1796589 | 8/2010 |
| EP | 2277474 A2 | 1/2011 |
| WO | 9737617 | 10/1997 |
| WO | 9737617 A1 | 10/1997 |
| WO | 9942528 A2 | 8/1999 |
| WO | 2006034340 | 3/2006 |
| WO | 2009132070 A2 | 10/2009 |
| WO | 2010068589 A1 | 6/2010 |
| WO | 2011056797 | 5/2011 |

OTHER PUBLICATIONS

Parodi et al., Annals of Vascular Surgery (1991) 5:491-499.
International Search Report dated Sep. 24, 2012 for PCT/GB2012/051236.
Office Action for European Application No. 12731617.2 dated Mar. 24, 2016.

* cited by examiner ns. Aneurysm occurs when a section of
natural blood vessel wall, typically of the aortic artery,
dilates and balloons outwardly. Whilst small aneurysms
cause little or no symptoms, larger aneurysms pose significant danger to a patient. Rupture of an aortic aneurysm can
occur without warning and is usually fatal, so significant
emphasis is placed on early diagnosis and treatment. With an
increasing ageing population, the incidence of aneurysm
continues to rise in western societies.

Provided that an aneurysm is diagnosed prior to rupture,
surgical treatment to repair the affected vessel wall is
effective. Surgical treatment of aneurysm involves the
replacement or reinforcement of the aneurismal section of
aorta with a synthetic graft or prosthesis under general
anaesthesia allowing the patient's abdomen or thorax to be
opened (see Parodi et al., Annals of Vascular Surgery (1991)
5:491-499). The patient will then have a normal life expectancy.

Surgical repair of aneurysm is however a major and
invasive undertaking and there has been much effort in
developing less invasive methods. Currently, aneurysm
repair generally involves the delivery by catheter of a fabric
or ePTFE graft which is retained at the required location by
deployment of metallic stent elements. The ability to deliver
the graft/stent device by catheter reduces the surgical intervention to a small cut-down to expose the femoral artery
and, in suitable circumstances, the device can be deployed
percutaneously. Catheter delivery is beneficial since the
reduced invasive nature of the procedure allows utilisation
of a local anaesthesic and leads to reduced mortality and
morbidity, as well as decreased recovery time. For example,
endovascular repair is typically used for repair of infra-renal
abdominal aortic aneurysms where the graft is placed below
the renal arteries. Many different types of devices useful for
endovascular repair are now available, for example a resiliently engaging endovascular element described in U.S. Pat.
No. 6,635,080 (Vascutek) or a tubular fabric liner having a
radially expandable supporting frame and a radiopaque
marker element stitched to the liner as disclosed in U.S. Pat.
No. 6,203,568 (Medtronic).

However, whilst the endovascular repair of aneurysms is
now accepted as the method of choice, the technique has
significant limitations and is not suitable for all patients.

As mentioned above, other vascular disorders are treatable by use of a vascular prosthesis. Examples include (but
are not limited to) occlusions, stenosis, vascular damage due
to accident or trauma, and the like. Vascular prostheses are
also used in by-pass techniques.

Endovascular techniques involve the delivery of the prosthesis by catheter. Since the internal lumen of the catheter
defines the maximum dimensions of the prosthesis to be
inserted, much effort has been expended in the design of
prostheses which can be packaged in a minimal volume, and
are easy to deploy once positioned at the required location.

One successful type of prosthesis consists of a stent graft
comprising a conduit formed from a flexible sleeve attached
to a rigid support or stent. The sleeve will typically be made
of a fabric (usually a knitted or woven fabric) of ePTFE,
PTFE, polyester (for example DACRON), polyethylene or
polypropylene and may optionally be coated to reduce
friction; discourage clotting or to deliver a pharmaceutical
agent. The fabric will generally be porous on at least one
surface to enable cell ingrowth. The stent may be balloon-expandable (eg. a PALMAZ stent made of rigid stainless
steel wire), but could also be self-expandable and formed of
a shape memory material, such as nitinol (a nickel-titanium
alloy). Numerous different stent designs are known in the art
(see for example braided stents described in EP 880949 or
wire zig-zag stents described in U.S. Pat. No. 4,580,568).

The stent grafts are inserted using a delivery catheter and,
once correctly located at the site requiring treatment, are
deployed by the withdrawal of a delivery sheath of the
delivery catheter. Balloon-expandable grafts are then caused
to expand in diameter by inflation of a balloon located within
the lumen of the graft. Self-expandable grafts radially
expand upon release from the delivery sheath. Irrespective
of the mode of expansion, once deployed, the stents hold the
graft in location by contact with the inner wall of the blood
vessel.

Since the stent will need to be compressed for loading into
the catheter and during delivery, in general terms, the stent
is formed from the minimum amount of material able to
maintain the patency of the sleeve lumen at the required
diameter.

One suitable stent design is formed from discrete rings of
a shape memory material, such as nitinol, attached to the
fabric sleeve at spaced intervals. Such a design fulfils the
requirements for minimal volume when packaged and, once
delivered, readily expands to maintain the patency of the
fabric lumen. However, stent grafts having such ring stent
elements have the disadvantage that the rings lack stability,
and in particular the rings have a tendency to rotate or tilt
relative to each other either during deployment or following
deployment.

The present invention provides a further, and separate,
stent element for stabilisation of ring stents on a stent graft
prosthesis. The term "stent element" as used herein refers to
a component for use in conjunction with a stent or stent
graft.

In one aspect, the present invention provides a stent
element having a central portion, with two arms extending
from the central position. The stent element can be formed
in a "V" shaped configuration or "Y" shaped configuration.

The use of a separate stent element according to the
invention (as opposed to a one-piece stent, for example EP
686379)) provides the advantage that there is no physical
join or weld to the upper and lower ring stents. Rather, in the
present invention, the stent element is independently
attached to the sleeve, and can therefore flex and bend
independently of the ring stents. The stent element of the
invention causes the two ring stents to become associated so
that the rings stabilise each other, thus reducing rotational
and/or tilting of the rings.

The arms of the stent element are each independently
resiliently deformable such that the angle formed between
the arms can be reduced for packaging and/or for delivery of the prosthesis, but can increase following deployment of the prosthesis on its release from the delivery sheath of the catheter.

The stent element for delivery of the invention has the advantage that it facilitates the folding of the ring stents. In addition to the arms folding together, they also twist (rotate along their length) to enable lower compaction forces. In one embodiment, the central portion of the "Y"-shape stent element is constrained between a ring stent and sleeve allowing the stent element a degree of rotational freedom and ability to move longitudinally relative to the ring stent and sleeve.

Thus, the stent element of the present invention is reversibly interchangeable between a first configuration and a second configuration. In the first configuration, suitable for packaging of the prosthesis in a catheter and for its delivery by endovascular techniques, the arms of the stent element are urged inwardly and the angle formed between the arms is decreased. For example the first configuration can be adopted due to the application of external pressure, such as a close fitting sleeve being placed externally over the stent graft. In the second configuration, which can be adopted once the external pressure caused by packaging of the device is removed, the arms spring resiliently outwardly adopting a more open configuration with a wider angle between the arms.

The central portion can be configured for attachment to the sleeve of the stent graft. For example the central portion can include an eye or aperture which can be attached to the sleeve of the stent graft, for example by sewing.

The distal end of each arm of the stent element (ie. the ends of each arm not attached to the central portion) can be configured for independent attachment to the sleeve of the stent graft. For example, the distal end of each arm can include an eye or aperture which can be attached to the sleeve of the stent graft, for example by sewing.

Optionally, the stent element of the invention has two, three or four arms extending outwardly from the central position. Where the stent element comprises four arms, it may be in an "X"-shaped configuration. In one embodiment, where the stent element has four arms, attachment of the distal ends of the arms to the sleeve is sufficient for attachment to the stent graft and it is not necessary to also attach the central portion of the stent element to the sleeve.

The stent element can be formed of any suitable biocompatible material having the necessary resilience to fold inwardly into a first folded configuration (ie. for packaging) and to adapt a second open configuration (ie. after deployment). Mention can be made of shape memory materials such as, for example, nitinol. Resilient polymers are also suitable, for example high durometer polyurethanes, or shape memory polymers described in WO 99/42528 or WO 2009/132070.

The stent element can be formed of any suitable biocompatible material having the necessary resilience to fold inwardly into a first folded configuration (ie. for packaging) and to adapt a second open configuration (ie. after deployment).

Mention can be made of shape memory materials such as, for example, nitinol. Resilient polymers are also suitable, particularly engineering high modulus polymers such as polyether ether ketone (PEEK). PEEK polymers with shape memory behaviour can be used.

The stent element of the invention can conveniently be formed by laser cutting, for example, by laser cutting from a planar sheet of material or cylindrical tube of material. This method allows a suitable degree of accuracy in forming the stent element.

Generally the planar sheet of material (for example nitinol) will be of 0.1 mm to 1.0 mm thickness, preferably from 0.2 mm to 0.9 mm, but other thicknesses including 0.3, 0.4, 0.5, 0.6, 0.7, 0.8 mm are also possible. The stent element can be formed as a one-piece construction by laser etching from a single piece of material, such as a nitinol sheet or cylinder.

In one embodiment, the stent element has a central portion having an aperture therein, and two resilient arms extending outwardly from the central portion, wherein each arm has an aperture in the end distal to the central portion. In this embodiment, the stent element can conveniently be in a "V"-shape or a "Y" shape. The stent element can conveniently be formed from nitinol, for example can be laser etched from a nitinol sheet.

In an alternative embodiment, the stent element has a central portion with four resilient arms extending outwardly therefrom, wherein each arm has an aperture in the end distal to the central portion. In this embodiment, the stent element can conveniently be in an "X" shape. The stent element can conveniently be formed from nitinol, for example can be laser etched from nitinol sheet. Where the stent element is "X" shaped, it can conveniently be formed from two "C" shaped portions, attached back-to-back, for example by sewing.

The stent element can be located between any two neighbouring ring stents in a stent graft.

The stent element can be positioned on the external face of the sleeve of the stent graft.

The stent element is located between two neighbouring ring stents and attached to the sleeve of the stent graft at or close to the location of each of the two neighbouring ring stents. Conveniently, the stent element is attached to the sleeve by sewing, but any other suitable means of attachment to the sleeve (eg. adhesive or heat bonding) could alternatively be used, provided some flexibility between the strut and fabric is maintained. We have found that sewing the stent element provides the necessary freedom of rotation relative to the ring stent(s) and graft sleeve to facilitate packing at low risk of fracture. Attachment to the sleeve (as opposed to the ring stents) reduces the potential for fracture of the stent and subsequent mechanical weakness.

In one embodiment, the central portion of the stent element is attached to the sleeve at or adjacent (for example immediately adjacent) to a first ring stent independently attached to the sleeve, and at least one arm of the stent element is attached to the sleeve at or adjacent (for example immediately adjacent) to a second ring stent independently attached to the sleeve.

In an alternative embodiment at least one arm of the stent element is attached to the sleeve at or adjacent (for example immediately adjacent) to a first ring stent independently attached to the sleeve, and the central element of the stent element is attached to the sleeve at or adjacent (for example immediately adjacent) to a second ring stent independently attached to the sleeve.

Conveniently, the stent element is located between a terminal ring stent and its immediate neighbour. This position has the advantage of increasing column stiffness at the end of the prosthesis, thereby increasing patency and improving the seal between the outer wall of the prosthesis and the inner surface of the natural blood vessel into which it has been located.

In one aspect, the present invention provides a stent graft comprising:

i) a sleeve having a first end and a second end with a lumen extending therethrough;

ii) at least two ring stents attached to the sleeve a pre-selected distance apart; and iii) a stent element having a central portion with at least two arms extending outwardly therefrom, wherein the stent element is attached to the sleeve so that it bridges the distance between the ring stents.

The sleeve can be flexible and is usually formed of a woven or knitted fabric. The sleeve will usually be substantially impervious to fluid. Optionally, at least one surface of the sleeve will be sufficiently porous to facilitate cell ingrowth. Suitable materials include polyester, polyethylene, polypropylene, ePTFE, PTFE and the like. The sleeve can be coated to reduce permeability or to deliver a biological agent.

For many intended purposes, the sleeve can conveniently be formed with a constant diameter. However tapered grafts (ie. where the diameter varies along its length) are also possible and are particularly useful for certain indications.

In a further aspect, the present invention provides an implantable prosthesis comprising:

i) a compliant and substantially fluid impervious tubular sleeve having a proximal end and a distal end with a conduit therethrough;

ii) a first ring stent formed from multiple windings of wire of a shape memory material, attached to said sleeve at a first location;

iii) a second ring stent formed from multiple windings of wire of a shape memory material, attached to said sleeve at a second location; and iv) a stent element having a central potion and at least two resilient arms extending therefrom, wherein a first portion of said stent element is attached to said sleeve at said first location, and wherein a second portion of said stent element is attached to said sleeve at said second location.

The ring stents can each be formed from nitinol wire and will typically include multiple windings of nitinol wire. Each ring stent can be attached to the external surface of the sleeve or to the internal (luminal) surface of the sleeve. Generally, it is more convenient to attach the ring stents to the external (non-luminal) surface of the sleeve.

Optionally, one of said ring stents is located at or close to the first or second ends of the sleeve. For example, although distances will vary with dimensions of the stent graft, one ring can conveniently be located from 0 to 2 cm from either the first or second end of the sleeve.

A suitable pre-selected distance for the closest point between the two ring stents is from 0.1 to 8 cm, preferably 0.5 to 5 cm, more preferably between 0.5 to 3 cm. One of skill in the art will however be aware that the pre-selected distance between the ring stents will depend upon factors such as the size (diameter and/or length) of the stent graft, its intended location in the patient, the patient's anatomy and medical condition.

The two ring stents can conveniently be immediate neighbours (ie. there will be no other ring stents attached to the sleeve in the space between them).

In the stent graft of the present invention, one portion of the stent element will be attached to the sleeve at or adjacent (for example immediately adjacent) to the location of one ring stent, and another portion of the stent element will be attached to the sleeve at or adjacent (for example immediately adjacent) to the other ring element. For example, the central portion can be attached to the sleeve at or adjacent to the second ring element and arm(s) of the stent element can be attached to the sleeve at or adjacent to the first ring element. Alternatively, this arrangement could be reversed.

In one embodiment, the stent element is formed from nitinol, preferably by laser etching from a planar sheet of nitinol typically 0.1 mm to 1 mm thick, for example 0.15 to 0.20 mm thick.

The stent graft can comprise a ring stent formed by multiple windings of resilient wire, for example nitinol wire. Optionally each ring stent can be formed from a plurality of strands of wire, but other designs of ring stents are also possible. The number of strands of wire can be varied according to the wire utilised and the size of graft. The number of strands wound can vary from 2 to 120 or even more, but would typically have 10 to 30 strands forming the ring stent. Any diameter wire which maintains the required resilience can be used. Suitable diameters can be selected from a range of 0.1 mm to 2 mm, for example 0.5 mm to 1 mm.

Conveniently each ring stent is attached to the sleeve by suitable attachment means, for example by mechanical means (such as sewing), by chemical means (such as adhesive) or by thermal means (for example heat bonding).

It is possible for the stent graft of the invention to include multiple ring stents, and the stent graft of the invention is not limited to any particular number of ring stents. For some embodiments the stent graft can have for example 3 to 15 ring stents but other numbers of ring stents are also possible depending on the graft length and diameter.

Optionally at least one ring stent of stent graft adopts a saddle shape in its open (deployed) configuration. A ring stent will be saddle shaped if the circumference of the ring stent is larger than the circumference of the outer surface of the sleeve of the stent graft and the ring stent is attached in a sinusoidal (saddle-shaped) configuration, having two peaks and troughs. A saddle-shape can be beneficial in improving flexibility of the stent graft. Optionally the stent element is located between two ring stents, one or both of which are saddle-shaped. Optionally the stent element is located between two ring stents, one of which is a terminal ring stent of the stent graft, this terminal ring stent being saddle-shaped.

The stent graft of the invention can include a single stent element. Alternatively the stent graft of the invention includes 2 or more stent elements. Where multiple stent elements are present, two stent elements can be located between the same two neighbouring ring stents, but diametrically opposite each other on the sleeve circumference.

Optionally the stent graft of the present invention includes stent elements located between ring stents at each end of the stent graft. Thus in this embodiment, at least one stent element is located between the terminal ring stent and its immediate neighbour at the first end of the sleeve and at least one stent element is located between the terminal ring stent and its immediate neighbour at the second end of the sleeve. In another embodiment at least one stent element may be located by protruding past the terminal ring at one end of the graft.

In a further aspect, the present invention provides a method of repairing a diseased vessel, said method comprising inserting a prosthesis comprising a flexible tubular conduit having at least two ring stents attached to the conduit at preselected locations thereon, and having a resilient stent element attached to each location.

The present invention further provides a method of treating a body lumen, said method comprising inserting a stent graft comprising:

i) a sleeve having a first end and a second end with a lumen extending therethrough;

ii) at least two ring stents attached to the sleeve a pre-selected distance apart; and iii) a stent element having a central portion with at least two arms extending outwardly therefrom, wherein the stent element is attached to the sleeve so that it bridges the distance between the ring stents.

In a further aspect, the present invention provides a method of treating a patient in need thereof, said method comprising implanting a prosthesis comprising:

i) a compliant and substantially fluid impervious tubular sleeve having a proximal end and a distal end with a conduit therethrough;

ii) a first ring stent formed from multiple windings of wire of a shape memory material, attached to said sleeve at a first location;

iii) a second ring stent formed from multiple windings of wire of a shape memory material, attached to said sleeve at a second location; and iv) a stent element having a central potion and at least two resilient arms extending therefrom, wherein a first portion of said stent element is attached to said sleeve at said first location, and wherein a second portion of said stent element is attached to said sleeve at said second location.

In a further aspect, the present invention provides a method of manufacturing a prosthesis suitable for implantation into the body, said method comprising:

(i) providing a flexible tubular conduit;
(ii) attaching a stent element to said conduit such that said stent element is attached at two distinct locations on said conduit;
(iii) attaching a first stent element to the conduit at or adjacent said first attachment point; and
(iv) attaching a second ring stent to said conduit at or adjacent said second attachment point.

The stent element can be attached to the exterior surface of said conduit. The first and second ring stents are also preferably attached to the exterior surface of said conduit and overlie at least a portion of the stent element at each discrete attachment point.

Whilst any means of attachment can be used to secure the stent elements and the ring stents to the conduit, conveniently the stent element is attached by sewing. Optionally, each of the ring stents is also attached by sewing.

Preferred or alternative features of each aspect or embodiment of the invention apply mutatis mutandis to each other aspect or embodiment of the invention, unless the context demands otherwise.

Figure 2:
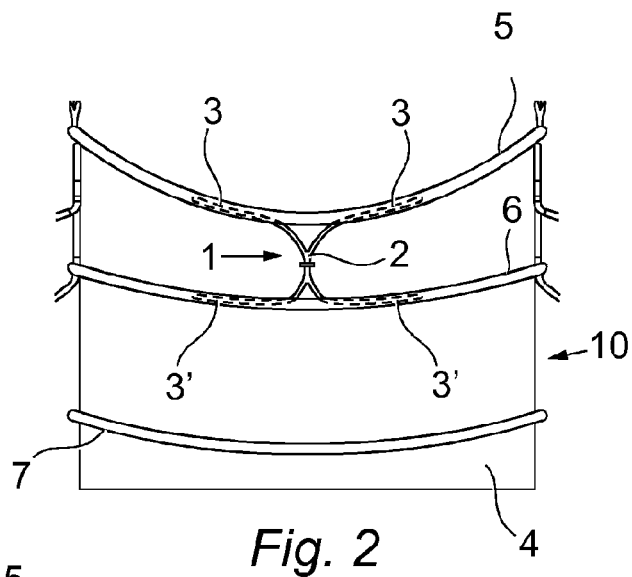
Figure 3A:
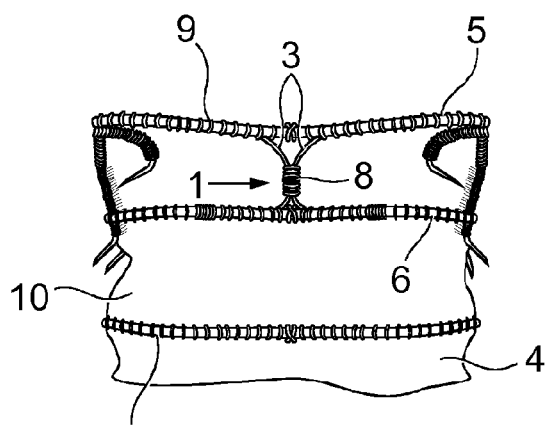
Figure 3B:
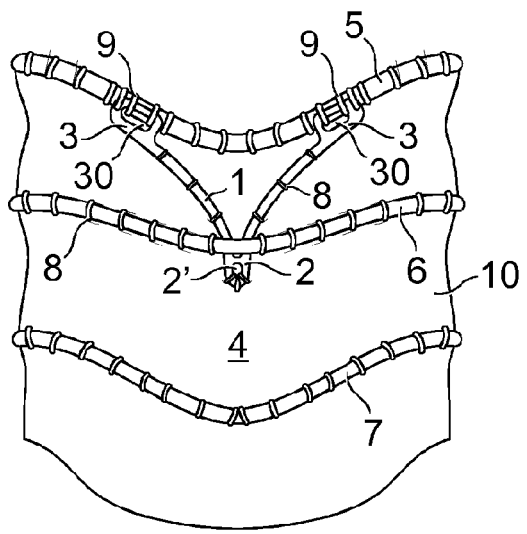
Figure 4A:
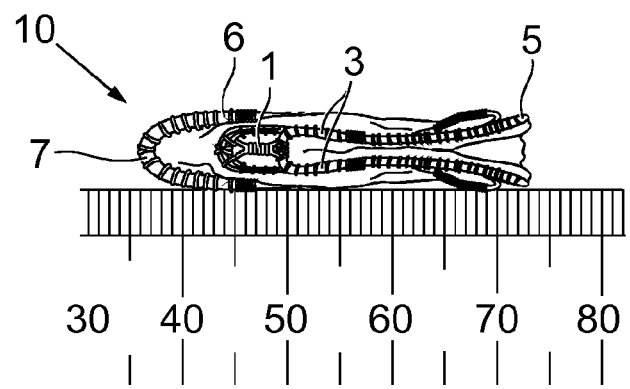
Figure 4B:
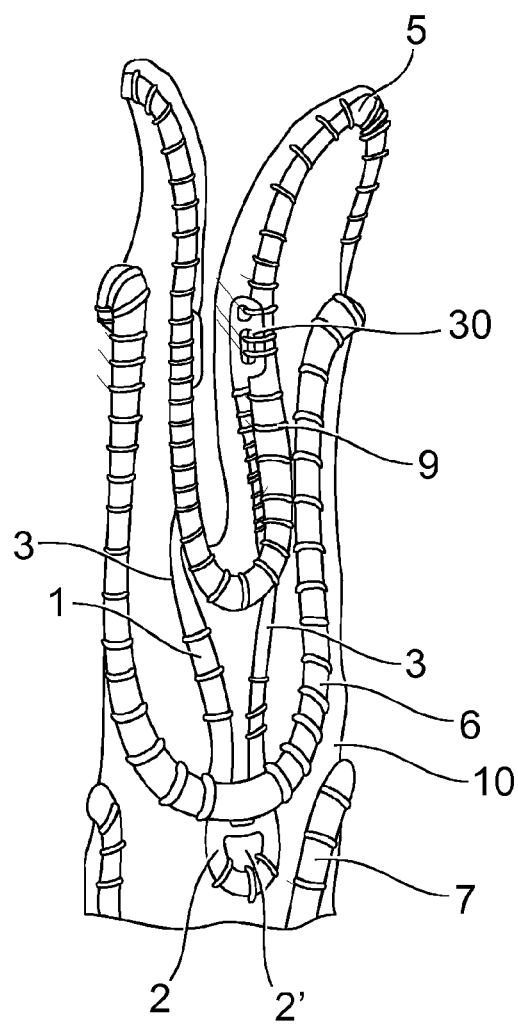
Figure 5:
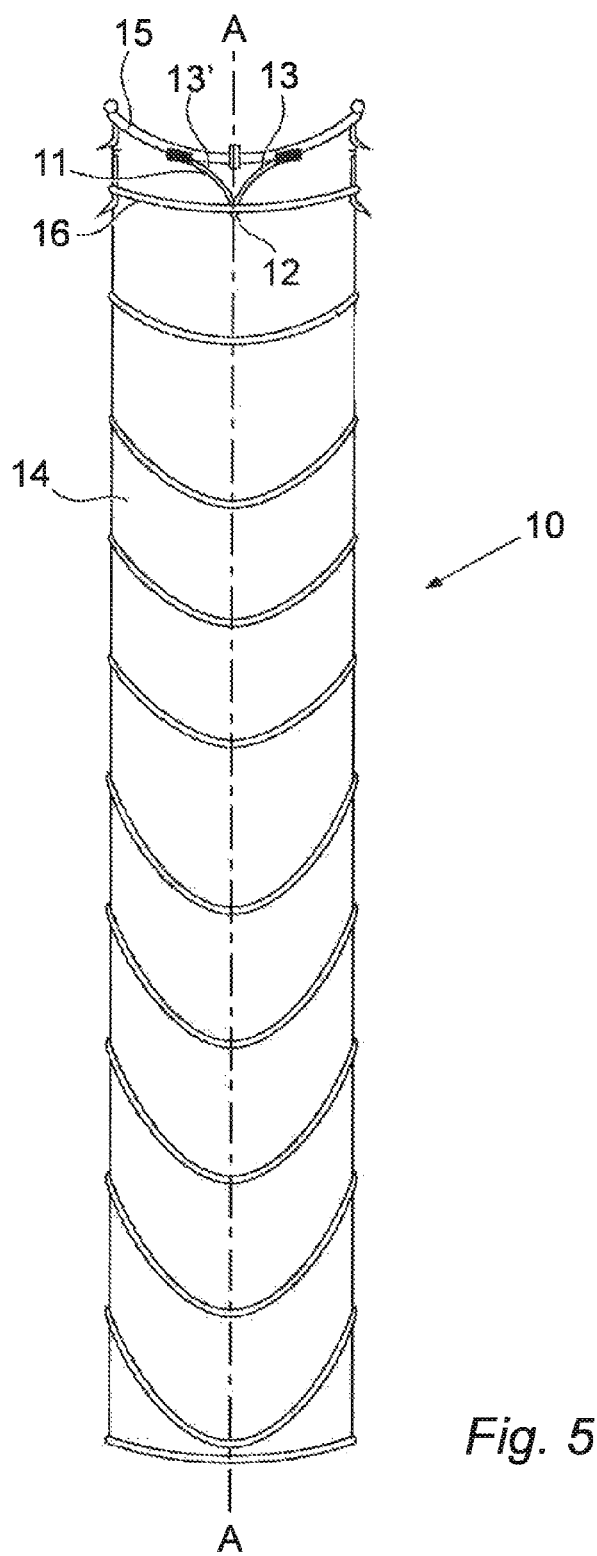

The present invention will now be further described by reference to the following figures, in which:

FIG. 1: is a schematic illustration of one embodiment of the stent element of the invention;

FIG. 2: is a schematic illustration of the stent element of FIG. 1 attached to one end of a stent graft;

FIG. 3A: is a schematic illustration of the stent graft of FIG. 2 showing attachment of the stent element and ring stents by sewing;

FIG. 3B: shows an alternative embodiment of the stent element of the invention attached to a stent graft;

FIG. 4A: is an end view of the stent graft of FIG. 3A shown in a folded configuration;

FIG. 4B: shows a side view of the stent graft of FIG. 3B shown in a folded configuration; and FIG. 5: shows a stent graft having a further embodiment of the stent element attached thereto.

Referring to the drawings, FIG. 1 shows a stent element (1) of the invention formed from nitinol and having a central portion (2) with four outwardly extending arms (3, 3, 3', 3'). As illustrated in FIG. 1, the stent element (1) is shown in an open configuration in which the upper pair of arms (3, 3) and lower pairs of arms (3', 3') have adopted a wide angle.

FIG. 2 shows the stent element (1) of FIG. 1 attached to a stent graft (10). Stent graft (10) is formed from a flexible tubular conduit or sleeve (4) having a number of ring stents attached thereto to maintain the patency of the sleeve lumen after deployment. Each ring stent can be formed from multiple windings of a resilient material, such as PEEK or nitinol wire. Only one end portion of stent graft (10) is illustrated, for convenience. In the end portion of stent graft (10) illustrated in FIG. 2, the stent graft (10) terminates with a first ring stent (5) which is spaced a pre-determined distance apart from its neighbouring ring stent (6). A further ring stent (7) is also illustrated. Further ring stents may be present on the portion of the stent graft not shown in FIG. 2. The stent element (1) of FIG. 1 is shown attached between ring stents (5) and (6). The locations of the arms of stent element (1) are indicated in FIG. 2, but are preferably located underneath the appropriate ring stents (5, 6). Thus, stent element (1) is attached to fabric sleeve (4) before attachment of the ring stents (5, 6). Fabric sleeve (4) is a woven or knitted flexible fabric which is generally impervious to fluid such as blood. Suitable materials include polyester, such as Dacron. Fabric sleeve (4) may be coated to reduce blood clotting, to reduce friction or to deliver a medicament. The stent graft (10) shown in FIG. 2 is depicted in the expanded (deployed) configuration.

FIG. 3A shows detail of the attachment of ring stents (5, 6, 7) to sleeve (4) in the stent graft (10) of FIG. 2 and also shows detail of the attachment of stent element (1) to the sleeve (4). As illustrated, the central portion of stent element (1) has been attached using stitches (8). Other forms of attachment are also possible. Additionally, the location of arms (3, 3) beneath ring stent (5) occurs prior to the stitching of ring stent (5) onto sleeve (4). Thus stitches (9) hold both arms (3, 3) and also ring stent (5) securely onto sleeve (4). Apart from stitches (9), there is no other attachment between the arms (3, 3) of stent element (1) and ring stent (5). Similarly stitches (9) hold arms (3', 3') and ring stent (6) securely onto the outer surface of sleeve (4). Again, apart from stitches (9) there is no attachment between arms (3', 3') of stent element (1) and ring stent (6). A second stent element can optionally be attached to stent graft (10) diametrically opposite the stent element (1) illustrated, and in the manner described above.

FIG. 3B shows detail of the attachment of ring stents (5, 6, 7) to sleeve 4 in a stent graft (10) and shows detail of the attachment of an alternative embodiment of the stent element (1) to sleeve (4). The central portion (2) of stent element (1) has been attached using stitches (8) and attachment is facilitated by an aperture or eye (2') in the central portion (2). The central portion (2) is located beneath the second ring stent (6) which is attached to sleeve (4) over central portion (2) of stent element (1). The second ring stent (6) is attached to sleeve (4) using stitches (8). The stent element (1) has two arms (3, 3) which extend outwardly from the central portion (2) so that stent element (1) has a "Y" shape configuration. Each arm (3) is attached to sleeve (4) underneath first ring stent (5) and is attached thereto using stitches (9) which simultaneously hold ring stent (5) onto sleeve (4). Attachment is facilitated by the aperture or eye (30) located at the end of each arm (3) through which stitches (9) can pass. Apart from stitches (9) there is no attachment between arms (3, 3) of stent element (1) and ring stent (5). A second stent element can optionally be attached to stent graft (10) diametrically opposite the stent element (1) illustrated, and in the manner described above.

FIG. 4A shows the end view of the stent graft (10) of FIG. 3A in a folded configuration, suitable for insertion into a catheter and deployment into the body lumen of a patient. A ruled scale (cm) is shown to provide an indication of exemplary size. In this configuration ring stents (5, 6, 7) and any other ring stents of graft (10) are compressed and will be held in that compressed form by an outer delivery sheath which forms part of the delivery catheter (not shown). As illustrated, arms (3, 3) of stent element (1) are bent by compression of ring stent (5), such that the tips of arms (3, 3) approach each other and the angle between these arms is decreased. Similarly, the folding of ring stent (6) into its compressed form causes arms (3', 3') to be urged together such that the tips of these arms are also brought close to each other and the angles between arms (3', 3') is decreased. Stent element (1) is formed of a resilient material, such as nitinol, which can tolerate such compression. Multiple windings of nitinol wire can be used to form each of the ring stents (e.g. ring stents 5, 6, 7). Upon deployment of the stent graft (10) (for example by removal of the delivery sheath located around the compressed stent graft), arms (3', 3') spring outwardly, together with ring stent (5) which adopts its open, annular configuration. Likewise, arms (3', 3') also spring outwardly together with ring stent (6) which adopts its open annular configuration.

FIG. 4B shows a side view of the stent graft (10) of FIG. 3B in a folded configuration, suitable for insertion into a catheter and delivery into the body lumen of a patient. In this configuration ring stents (5, 6, 7) and any other rings stents of graft (10) are compressed and will be held in that compressed form by an outer delivery sheath which forms part of the delivery catheter (not shown). As illustrated, arms (3, 3) of stent element (1) are bent by compression of ring stent (5) such that the tips of arms (3, 3) approach each other and the angle between these arms is decreased. Stent element (1) is formed of a resilient material such as nitinol or a shape memory polymer and can tolerate such compression without fracture. Each arm (3) remains securely attached to ring stent (5) by stitches (9) and is facilitated eye or loop (30) located at the terminal end of each arm (3). FIG. 4B illustrates that the stent element (1) facilitates the folding of the ring stents (5, 6). In addition to arms (3, 3) folding together, they also twist (rotate along their length) to enable lower compaction forces. The central limb element (2) of the "Y"-shape is constrained between stent (6) and sleeve (4) allowing the stent element (1) a degree of rotational freedom and ability to move longitudinally relative to ring stent (6) and sleeve (4). Upon deployment of the stent graft (10) (for example by removal of the delivery sheath located around the compressed stent graft), arms (3', 3') spring outwardly, together with ring stent (5) which adopts its open, annular configuration.

FIG. 5 shows an alternative embodiment of the stent element (11) of the present invention in which stent element (11) comprises a central portion (12) with two flexible resilient arms (13, 13') extending outwardly therefrom. Stent graft (10) comprises a flexible sleeve (14), for example formed of woven polyester such as Dacron. As illustrated, stent graft (10) comprises twelve separate ring stents, each spaced a predetermined distance apart. Central portion (12) of stent element (11) is attached to sleeve (14) at or adjacent to the location of ring stent (16). The resilient arms (13, 13') of stent element (11) are attached to sleeve (14) at or adjacent to the location of ring stent (15). Ring stents (15) and (16) are immediate neighbours on stent graft (10) and are attached to the outer surface of sleeve (14). Stent element (11) is shown in its open (deployed) configuration and has a large angle between resilient arms (13, 13'). In its compressed configuration (not shown) the tips of arms (13, 13') will be urged together, for example by applying external pressure, such that the angle between arms (13, 13') is decreased. Suitably, stent element (11) is attached at central portion (12) and at the tips of arms (13, 13') by sewing using suture material. Optionally central portion (12) includes an aperture or loop (not shown) which can be used to secure central portion (12) to the outer surface of sleeve (14). Similarly, each of arms (13, 13') conveniently includes an aperture or loop (not shown but equivalent to loop (30) in FIG. 3B) which can be used to secure arms (13, 13') to the outer surface of sleeve (14) by sewing, for example using sutures. Ring stents (15, 16) are then located on the outer surface of sleeve (14) and again are suitably secured to that surface. Conveniently, the ring stents can be secured by sewing.

As illustrated in FIG. 5, the terminal ring stent (15) has a saddle shape with a trough approximately aligned with the central portion (12) of stent element (11) on the longitudinal axis A-A. As illustrated, ring stent (16) is of a more annular configuration.

A second stent element can optionally be attached to stent graft (10) diametrically opposite the stent element (11) illustrated, and in the manner described above.

All documents referred to in this specification are herein incorporated by reference. Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:
1. A stent graft comprising:
   i) a sleeve having a first end and a second end with a lumen extending therethrough;
   ii) at least two unconnected ring stents attached to the sleeve a pre-selected distance apart; and
   iii) a stent element having a central portion with at least two arms extending outwardly therefrom, wherein the stent element is attached to the sleeve so that it bridges the pre-selected distance between the ring stents.

2. The stent graft of claim 1 wherein said stent element is in a V-shaped or Y-shaped configuration.

3. The stent graft of claim 1 wherein said stent element comprises from four arms in an X-shaped configuration.

4. The stent graft of claim 1 wherein the arms of the stent element are each resiliently deformable.

5. The stent graft of claim 1 wherein the stent element is formed from nitinol.

6. The stent graft of claim 1 wherein the ring stents are formed from multiple windings of nitinol wire.

7. The stent graft as claimed in claim 1, wherein the stent element is configured to flex and bend independently of the at least two ring stents.

8. The stent graft as claimed in claim 1, wherein at least one of the at least two arms of the stent element bridges the pre-selected distance between the ring stents.

9. An implantable prosthesis comprising:
  i) a compliant and substantially fluid impervious tubular sleeve having a proximal end and a distal end with a conduit therethrough;
  ii) a first ring stent formed from multiple windings of wire of a shape memory material, attached to said sleeve at a first location;
  iii) a second ring stent formed from multiple windings of wire of a shape memory material, attached to said sleeve at a second location; and
  iv) a stent element having a central portion and at least two resilient arms extending therefrom, wherein a first portion of said stent element is attached to said sleeve at said first location, and wherein a second portion of said stent element is attached to said sleeve at said second location,
  wherein the first ring stent and the second ring stent are unconnected ring stents.

10. The prosthesis of claim 9 wherein said stent element is in a V-shaped or Y-shaped configuration.

11. The prosthesis of claim 9 wherein said stent element comprises from four arms in an X-shaped configuration.

12. The prosthesis of claim 9 wherein the arms of the stent element are each resiliently deformable.

13. The prosthesis of claim 9 wherein the stent element is formed from nitinol.

14. The prosthesis of claim 9 wherein the ring stents are formed from multiple windings of nitinol wire.

15. A method of treating a body lumen, said method comprising inserting a stent graft comprising:
  i) a sleeve having a first end and a second end with a lumen extending therethrough;
  ii) at least two unconnected ring stents attached to the sleeve a pre-selected distance apart; and
  iii) a stent element having a central portion with at least two arms extending outwardly therefrom, wherein the stent element is attached to the sleeve so that it bridges the distance between the ring stents.

16. The method as claimed in claim 15 wherein said stent element has a V-shaped or Y-shaped configuration.

17. The method as claimed in claim 15 wherein said stent element has four arms in an X-shaped configuration.

18. The method as claimed in claim 15 the arms of the stent element are each resiliently deformable.

19. The method as claimed in claim 15 wherein the stent element is formed from nitinol.

20. A method of treating a patient in need thereof, said method comprising implanting a prosthesis comprising:
  i) a compliant and substantially fluid impervious tubular sleeve having a proximal end and a distal end with a conduit therethrough;
  ii) a first ring stent formed from multiple windings of wire of a shape memory material, attached to said sleeve at a first location;
  iii) a second ring stent formed from multiple windings of wire of a shape memory material, attached to said sleeve at a second location; and
  iv) a stent element having a central portion and at least two resilient arms extending therefrom, wherein a first portion of said stent element is attached to said sleeve at said first location, and wherein a second portion of said stent element is attached to said sleeve at said second location,
  wherein the first ring stent and the second ring stent are unconnected ring stents.

21. The method as claimed in claim 20 wherein said stent element has a V-shaped or Y-shaped configuration.

22. The method as claimed in claim 20 wherein said stent element has four arms in an X-shaped configuration.

23. The method as claimed in claim 20 the arms of the stent element are each resiliently deformable.

24. The method as claimed in claim 20 wherein the stent element is formed from nitinol.

25. A method of manufacturing a prosthesis suitable for implantation into the body, said method comprising:
  (i) providing a flexible tubular conduit;
  (ii) attaching a stent element to said conduit such that said stent element is attached at two distinct locations on said conduit;
  (iii) attaching a first stent element to the conduit at or adjacent said first attachment point; and
  (iv) attaching a second ring stent to said conduit at or adjacent said second attachment point,
  wherein the first ring stent and the second ring stent are unconnected ring stents.

26. The method as claimed in claim 25 wherein said stent is attached to the conduit by stitching.

27. The method as claimed in claim 25 wherein said stent element has a V-shaped or Y-shaped configuration.

28. The method as claimed in claim 25 wherein said stent element has four arms in an X-shaped configuration.

29. The method as claimed in claim 25 wherein the stent element is formed from nitinol.

30. A stent graft comprising:
  a sleeve having a first end and a second end with a lumen extending therethrough;
  at least two ring stents attached to the sleeve a pre-selected distance apart; and
  a stent element having a central portion with at least two arms extending outwardly therefrom,
  wherein the stent element is attached to the sleeve such that it bridges the pre-selected distance between the at least two ring stents, and
  wherein the at least two ring stents are separate and distinct ring stents, and wherein the stent element is a separate and distinct component from the at least two ring stents.

31. A stent graft comprising:
  a sleeve having a first end and a second end with a lumen extending therethrough;
  at least two ring stents attached to the sleeve a pre-selected distance apart; and
  a stent element having a central portion with at least two arms extending outwardly therefrom,
  wherein the stent element is attached to the sleeve such that it bridges the pre-selected distance between the at least two ring stents, and
  wherein the stent element is only attached to the sleeve.

32. A stent graft comprising:
  a sleeve having a first end and a second end with a lumen extending therethrough;
  at least two ring stents attached to the sleeve a pre-selected distance apart; and
  a stent element having a central portion with at least two arms extending outwardly therefrom,
  wherein the stent element is attached to the sleeve such that it bridges the pre-selected distance between the at least two ring stents, and,
  wherein the stent element is not directly coupled to the at least two ring stents.

* * * * *